United States Patent
Mera et al.

(10) Patent No.: US 6,425,741 B1
(45) Date of Patent: Jul. 30, 2002

(54) CLUTCHLESS VARIABLE-CAPACITY TYPE COMPRESSOR

(75) Inventors: Minoru Mera; Kazuya Kimura; Hiroshi Uneyama, all of Kariya (JP)

(73) Assignee: Kabushiki Kaisha Toyoda Jidoshokki Seisakusho, Kariya (JP)

( * ) Notice: Subject to any disclaimer, the term of this patent is extended or adjusted under 35 U.S.C. 154(b) by 0 days.

(21) Appl. No.: 09/616,087

(22) Filed: Jul. 14, 2000

(30) Foreign Application Priority Data

Aug. 5, 1999 (JP) .......................................... 11-222035

(51) Int. Cl.$^7$ ................................................. F04B 1/26
(52) U.S. Cl. ..................................... 417/222.2; 417/269
(58) Field of Search ............................. 417/222.2, 269

(56) References Cited

U.S. PATENT DOCUMENTS

| | | | | |
|---|---|---|---|---|
| 5,915,928 A | * | 6/1999 | Murase et al. | 417/269 |
| 5,941,157 A | * | 8/1999 | Tokumasu | 92/12.2 |
| 6,076,449 A | * | 6/2000 | Kawaguchi et al. | 92/12.2 |
| 6,152,845 A | * | 11/2000 | Okada et al. | 474/93 |
| 6,203,284 B1 | * | 3/2001 | Kawaguchi et al. | 417/222.2 |

FOREIGN PATENT DOCUMENTS

| EP | 0867617 A2 | * | 9/1998 |
|---|---|---|---|
| JP | 10-205446 A | | 8/1998 |

* cited by examiner

*Primary Examiner*—Charles G. Freay
*Assistant Examiner*—William Rodriguez
(74) *Attorney, Agent, or Firm*—Woodcock Washburn LLP (57) ABSTRACT

A variable capacity type compressor has a swash plate which can incline with respect to the drive shaft. An angle decreasing spring urges the swash plate to decrease the inclination angle and a return spring urges the swash plate to increase the inclination angle from the minimum inclination angle beyond the limit angle. The minimum inclination angle is smaller than a limit angle at which the swash plate can be assuredly returned in the direction to increase the inclination angle by a reaction force of the discharge pressure, and the angle decreasing spring balances with the return spring at an angle greater than the limit angle. A minimum spring load ($F_0$) of the return spring is greater than 20N. A maximum spring load ($F_{100}$) of the angle decreasing spring is $F_{100}(N)=(180\pm30)-4\times(V_D-120)$.

16 Claims, 4 Drawing Sheets

A: ANGLE DECREASING DIRECTION
B: ANGLE INCREASING DIRECTION

A: ANGLE DECREASING DIRECTION
B: ANGLE INCREASING DIRECTION

CLUTCHLESS VARIABLE-CAPACITY TYPE COMPRESSOR

BACKGROUND OF THE INVENTION

1. Field of the Invention

The present invention relates to a swash-plate type variable-capacity type compressor for use in a vehicle air conditioner or the like.

2. Description of the Related Art

A compressor is incorporated in a refrigerating circuit, for a car air-conditioning system, for compressing coolant gas. A known swash plate type variable capacity type compressor comprises a housing having cylinder bores, a crank chamber, a suction chamber, and a discharge chamber formed therein, and pistons reciprocatingly arranged in the cylinder bores. A drive shaft is rotatably supported by the housing and driven by an external drive source, and a swash plate is supported by the drive shaft so that the swash plate is rotatable with the drive shaft and can incline with respect to the drive shaft, with shoes provided on the swash plate to convert the rotation of the drive shaft into the reciprocating motion of the pistons. In this compressor, a capacity control valve is provided for controlling the pressure in the crank chamber for changing a discharge capacity from the cylinder bores to the discharge chamber by the reciprocating motion of the pistons based on an inclination angle of the swash plate.

The conventional compressor is usually operatively coupled to a car engine as an external drive source via a belt and a magnetic clutch, so that the compressor is connected to the engine only when a refrigerating load occurs to effect a compressing operation.

However, if the magnetic clutch is provided in the compressor, problems arise in that the total weight increases, the production cost increases, and power is consumed for operating the magnetic clutch. To eliminate these drawbacks, there has recently been proposed a so-called clutchless swash plate type variable capacity type compressor which is directly coupled to an external drive source without a magnetic clutch interposed between the engine and the compressor, so that the compressor is normally driven while the external drive source is operating (for example, refer to Japanese Unexamined Patent Publication (Kokai) No. 10-205446). In the compressor disclosed in the above-described publication, a swash plate is arranged so that it can incline with respect to a drive shaft directly coupled to the external drive source, and a minimum inclination angle of the swash plate is maintained to provide a minimum discharge capacity. Therefore, in this compressor, it is possible to realize reduction of weight as well as to minimize power consumption of the external drive source, by directly coupling the compressor to the drive source without any magnetic clutch.

The problem of the conventional compressor is how to reduce power consumption of the external drive source. For example, power consumption reduction is required when the external drive source is being driven and the magnetic clutch is transferring the drive force of the external drive source, in the case where the magnetic clutch is provided and when the external drive source is being driven and the refrigerating function is stopped, for example, by turning off the operating switch of the car air conditioning device, in the case where the magnetic clutch is not provided.

That is, the control of the discharge capacity of the compressor is generally carried out by controlling the pressure (Pc) in the crank chamber using the capacity control valve. In particular, the inclination angle of the swash plate decreases and the discharge capacity decreases, when the pressure (Pc) in the crank chamber is raised by introducing the coolant gas from the discharge chamber having a high discharge pressure (Pd) into the crank chamber. On contrary, the inclination angle of the swash plate increases and the discharge capacity increases, when the pressure (Pc) in the crank chamber is lowered by introducing the coolant gas from the crank chamber into the suction chamber having the low suction pressure (Ps). In this constitution, it is necessary for the swash plate to be returned from the position of the minimum inclination angle to the position of the maximum inclination angle, when the pressure (Pc) in the crank chamber is lowered.

However, in the conventional compressor, if the minimum inclination angle is set to a value close to zero degrees, the compression action is not substantially carried out and the reaction force of the discharge pressure is not provided, so the swash plate is not assuredly returned to increase the inclination angle thereof. Therefore, it is not possible to set the minimum inclination angle to a value close to zero degrees in order to ensure the return of the swash plate to increase the inclination angle, and it is necessary to set the minimum inclination angle to a value in the range of 3 to 5 degrees, for example. In this way, it is necessary to maintain such a condition that the compression action of the compressor is slightly carried out even if the swash plate is at the minimum inclination angle, so that the reaction force of the discharge pressure contributes to return the swash plate to increase the inclination angle. By arranging the compressor in this way, the return of the swash plate to increase the inclination angle is ensured, in association with the decrease of the pressure (Pc) in the crank chamber.

In this case, when the swash plate is brought into the position of the minimum inclination angle, the swash plate continues to carry out the compressing action at the minimum inclination angle so that the reaction force of the discharge pressure normally acts on the swash plate, resulting in a problem that the power of the external drive source is consumed, even though it is small. It is therefore necessary to select the inclination angle of the swash plate during the minimum capacity operation to be as small as possible to provide the reaction force of the discharge pressure to reduce the power consumption of the air conditioning system while it is turned off, but it is not possible to return the swash plate from the minimum capacity operation (minimum inclination angle) if the reaction force of the discharge pressure is too small. In this manner, the reduction of the power consumption during the minimum capacity operation and securing returnability of the swash plate to increase the inclination angle are contradictory requirements, and it is necessary to control the minimum discharge capacity (minimum inclination angle) with high accuracy to meet these two requirements, so the production is difficult and the production costs increase.

In this connection, it is conceivable to arrange the compressor such that the minimum inclination angle is smaller than a limit angle at which the swash plate can be assuredly returned to increase the inclination angle by a reaction force of the discharge pressure, a return spring urging the swash plate so as to increase the inclination angle of the swash plate from the minimum inclination angle beyond the limit angle, and the urging force of the angle decreasing spring balancing with the urging force of the return spring at an angle greater than the limit angle. By this arrangement, it is possibly to satisfy two requirements, i.e., the reduction of the power consumption during the minimum capacity operation and securing returnability of the swash plate to increase the inclination angle, and it is not necessary to control the minimum discharge capacity (minimum inclination angle), and to realize the reduction of the production costs.

However, in experiments by the inventors, it was found that the above described advantageous effect is not satisfactory if the angle decreasing spring and the return spring are not appropriately selected. In particular, in the case where the discharge chamber is connected to the external refrigerating circuit via a check valve, it is important to allow the swash plate to increase the inclination angle, since the discharge pressure (Pd) is apt to be maintained constant and the discharge capacity can be more reliably and easily decreased.

SUMMARY OF THE INVENTION

In view of the above described prior art problems, an object of the present invention is to provide a swash plate type variable capacity type compressor by which the power consumption can be reduced, the swash plate can be assuredly returned to increase the inclination angle, and the production cost can be reduced.

According to one aspect of the present invention, there is provided a variable capacity type compressor comprising a housing having cylinder bores, a crank chamber, a suction chamber, and a discharge chamber formed therein. Pistons are reciprocatingly arranged in the cylinder bores, a drive shaft is rotatably supported by the housing and driven by an external drive source, and a swash plate is supported by the drive shaft so that the swash plate is rotatable with the drive shaft and can incline with respect to the drive shaft to convert the rotation of the drive shaft into the reciprocating motion of the pistons. A device such as a capacity control valve is arranged to control the pressure in the crank chamber for changing a discharge capacity, from the cylinder bores to the discharge chamber by the reciprocating motion of the pistons, based on an inclination angle of the swash plate. The swash plate is able to incline between a minimum inclination angle and a maximum inclination angle, the minimum inclination angle being smaller than a limit angle at which the swash plate can be assuredly returned in a direction to increase the inclination angle by a reaction force of the discharge pressure. An angle decreasing spring urges the swash plate so as to decrease the inclination angle of the swash plate from the maximum inclination angle toward the minimum inclination angle, and a return spring urges the swash plate so as to increase the inclination angle of the swash plate from the minimum inclination angle beyond the limit angle. The urging force of the angle decreasing spring balances the urging force of the return spring at an angle greater than the limit angle. A minimum spring load ($F_0$) of the return spring applied to the swash plate at a minimum discharge capacity is greater than 20N.

In this compressor, the compressing action of the compressor becomes smaller or substantially zero while the swash plate is at the minimum inclination angle, so the power consumption of an external drive source is reduced. The swash plate can rotate at the inclination angle greater than the limit angle when the compressor is restarted since and the urging force of the angle decreasing spring balances with the urging force of the return spring, so that the swash plate can be reliably returned in the direction to increase the inclination angle.

In the inventor's experiments, it has been found that an advantageous effect of the compressor can be ensured, as expected, if the minimum spring load ($F_0$) of the return spring applied to the swash plate at a minimum discharge capacity is greater than 20N. The upper limit of the minimum spring load ($F_0$) can be determined in accordance with the product of inertia of the swash plate and other members which rotate with the drive shaft, and the power consumption for driving the drive shaft becomes greater as far as a typical swash plate is used.

Also, according to another aspect of the present invention, there is provided a variable capacity type compressor comprising a fundamental arrangement similar to the above described compressor. The compressor in this embodiment includes the feature that a maximum spring load ($F_{100}$) of the angle decreasing spring applied to the swash plate at a maximum discharge capacity is determined by the following relationship:

$$F_{100}(N)=(180\pm30)-4\times(V_D-120) \qquad (1)$$

where $V_D$ is the displacement of the compressor.

In this compressor too, it has been found that an advantageous effect of the compressor can be ensured, as expected, if the maximum spring load ($F_{100}$) is determined by the above described relationship. The upper limit of the maximum spring load ($F_{100}$) is determined by the relationship, $F_{100}(N)=(180+30)-4\times(V_D-120)$, and the lower limit of the maximum spring load ($F_{100}$) is determined by the relationship, $F_{100}(N)=(180-30)-4\times(V_D-120)$. The lower limit of the maximum spring load ($F_{100}$) affects hunting of the swash plate.

Preferably, the angle decreasing spring is arranged around the drive shaft between a first fixed point and the swash plate, and the return spring urging the swash plate is arranged around the drive shaft between a second fixed point and the swash plate, the second fixed point being on the opposite side to the first fixed point with respect the swash plate.

Preferably, the compressor further comprises a lug plate fixed to the drive shaft in the crank chamber for rotation with the drive shaft, the swash plate being coupled to the lug plate so that the swash plate is rotatable with the lug plate and the swash plate is axially movable with respect to the lug plate, the lug plate providing the first fixed point.

Preferably, the compressor further comprises a circlip fixed to the drive shaft, the circlip providing the second fixed point.

Preferably, the discharge capacity when the urging force of the angle decreasing spring balances the urging force of the return spring is in the range from 3 to 10% of the maximum discharge capacity. In this constitution, the above described advantageous effect is further reliably ensured.

Preferably, the compressor is operatively coupled to an external drive source in a clutchless manner. In this case, the above described advantageous effect is further reliably ensured. In the clutchless compressor, the power is always transferred to the compressor as far as the external drive source is being driven, so the effect of reducing the power consumption is remarkable. Also, the weight of the compressor can be reduced.

Preferably, the compressor further comprises a check valve, the discharge chamber being connected to an external refrigerating circuit via the check valve. In this case, the effect of returning the swash plate is reliably ensured. In this compressor, it is possible to prevent the coolant gas from flowing in reverse, so it is possible to prevent the coolant liquid from staying in the compressor and to prevent an excessive rise in the pressure and the temperature in the compressor, to thereby improve durability of the compressor.

Preferably, the device controlling the pressure in the crank chamber comprises a first passage connecting the discharge chamber to the crank chamber, a second passage connecting the suction chamber to the crank chamber and a valve arranged in at least one of the first and second passages.

BRIEF DESCRIPTION OF THE DRAWINGS

The present invention will become more apparent from the following description of the preferred embodiments, with reference to the accompanying drawings, in which.

DESCRIPTION OF THE PREFERRED EMBODIMENTS

The present invention will now be described with reference to the preferred embodiment shown in the attached drawings.

Figure 1:
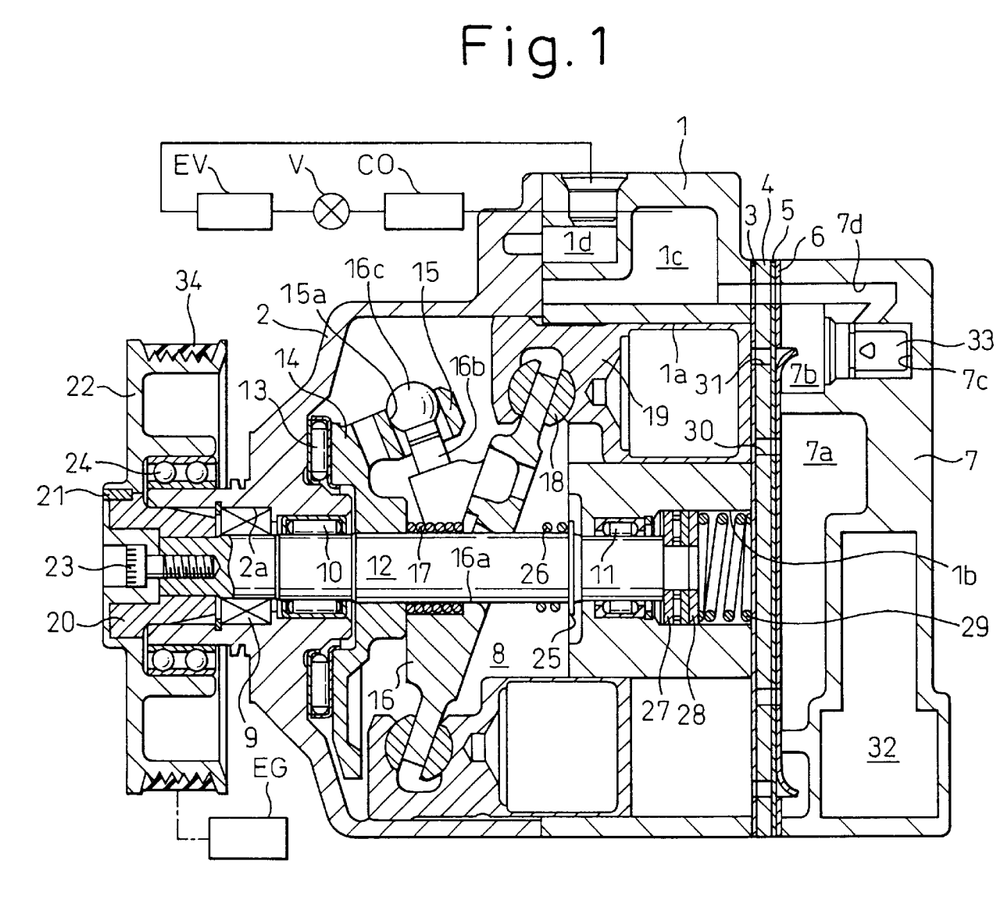
FIG. 1 is a longitudinal sectional view of a variable capacity type compressor according to an embodiment of the present invention, illustrating a swash plate in the maximum inclination angle.
Figure 2:
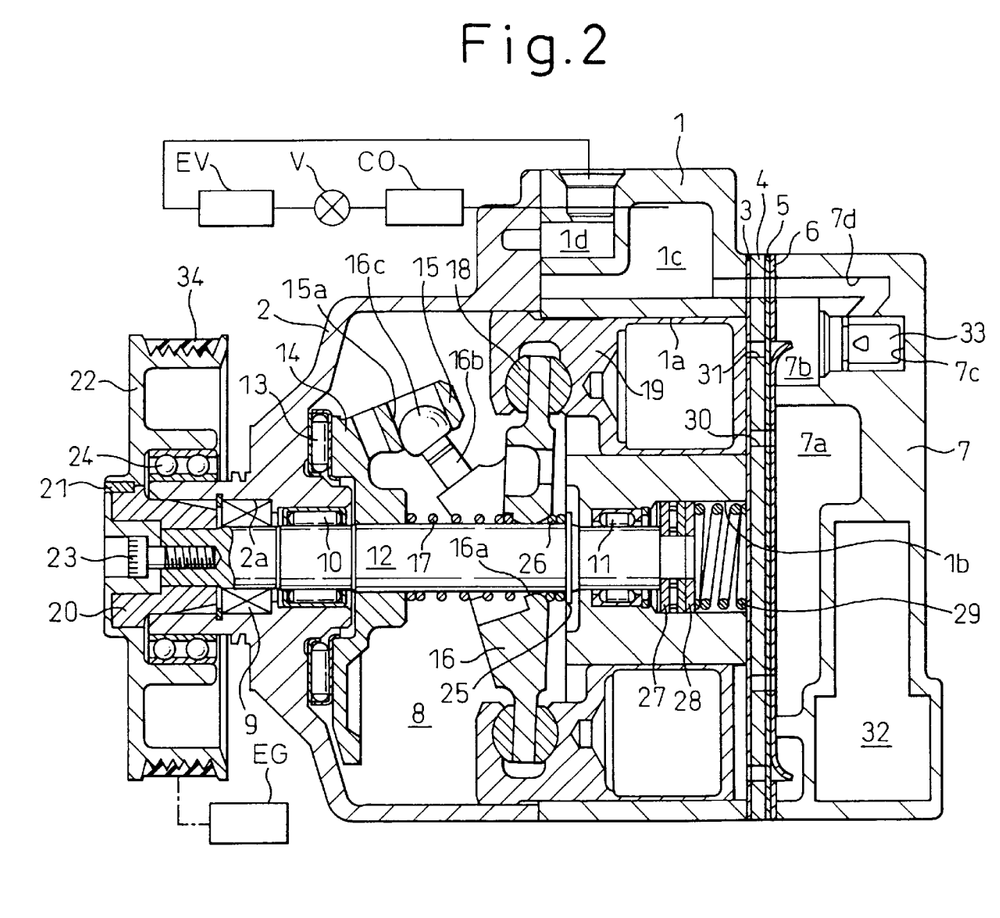
FIG. 2 is a longitudinal sectional view of the variable capacity type compressor of FIG. 1, illustrating the swash plate in the minimum inclination angle.

As shown in FIGS. 1 and 2, the compressor has a housing comprising a cylinder block 1, a cup-shaped front housing 2 attached to the front end of the cylinder block 1, and a rear housing 7 attached to the rear end of the cylinder block 1 via a valve assembly comprising a suction valve plate 3, a central valve plate 4, a discharge valve plate 5 and a retainer plate 6. The cylinder block 1, the front housing 2 and the rear housing 7 are made of an aluminum-type metal.

The cylinder block 1 has six cylinder bores 1a, an axial bore 1b, a muffler chamber 1c and a pre-suction chamber 1d. The front housing 2 has an axial bore 2a. The rear housing 7 has a suction chamber 7a, a discharge chamber 7b, an accommodating chamber 7c, and a discharge passage. The suction valve plate 3 has suction valve elements, the central valve plate 4 has valve holes, the discharge valve plate 5 has discharge valve elements, and the retainer plate has retainer elements, in accordance with the cylinder bores.

A drive shaft 12 is rotatably arranged in a crank chamber 8, which is formed in the front end portion of the cylinder block 1 and the front housing 2, and supported by a shaft seal device 9 and a radial bearing 10 in the axial bore 2a and a radial bearing 11 in the axial bore 1b.

A swash plate 16 is arranged in the crank chamber 8 and mounted to the drive shaft 12. The drive shaft 12 extends through a through-hole 16a of the swash plate 16. A lug plate 14 is fixed to the drive shaft 12 in the crank chamber 8, and a thrust bearing 13 is interposed between the lug plate 14 and the front housing 2. A pair of arms 15 project rearward from the lug plate 14, each of the arms 15 having a guide bore 15a having a cylindrical inner wall. A pair of guide pins 16b extend from the front end of the swash plate 16 toward the pair of arms 15, respectively. Each guide pin 16b has a guide portion 16c having a spherical outer surface at the tip end thereof, which is rotatably and slidably engaged in the guide bore 15a.

An angle decreasing spring 17 is disposed around the drive shaft 12 between the swash plate 16 and the lug plate 14 to urge the swash plate 16 toward the rear housing 7 so as to decrease the inclination angle of the swash plate 17 from the maximum inclination angle toward the minimum inclination angle.

A plurality of hollow pistons 19 are reciprocatingly arranged in the cylinder bores 1a and engaged with the peripheral portion of the swash plate 16 by pairs of shoes 18 on the front and rear surfaces of the swash plate 16, respectively. In this embodiment, the displacement ($V_D$) of the compressor is 120 CC.

A boss 20 is fitted on a portion of the drive shaft 12 extending forward from the front housing 2 by spline engagement, and a pulley 22 is fixed to the boss 20 by a key 21. The pulley 22 is fixed to the drive shaft 12 with a bolt 23 and is rotatably supported by the front housing 2 through a ball bearing 24. A belt 34 is wound on the pulley 22, and coupled to an engine EG of a car as an external drive source.

A return spring 26 is arranged around the drive shaft 12 at a position slightly behind the swash plate 16 and secured by a circlip 25, to receive the swash plate 16 when the swash plate 16 moves to the right in FIG. 1. A thrust bearing 27 and a washer 28 are provided in the axial bore 1b of the cylinder block 1 at the rear end of the drive shaft 12, and a spring 29 is disposed between the washer 28 and the suction valve plate 3.

Therefore, the swash plate 16 is rotatable with the drive shaft 12 to carry out a known compression operation, and can incline with respect to the drive shaft 12 to change the capacity of the compressor. The swash plate 16 can incline between a maximum inclination angle in which discharge capacity of the compressor is the maximum (FIG. 1) and a minimum inclination angle in which discharge capacity of the compressor is the minimum (FIG. 2).

The minimum inclination angle of the swash plate 16 is determined so that it is smaller than a limit angle at which the swash plate 16 can assuredly return in the direction to increase the inclination angle by a reaction force of the discharge pressure. The urging force of the angle decreasing spring 17 balances with the urging force of the return spring 26 at an angle greater than the limit angle. In addition, the return of the swash plate 16 from the condition of the minimum inclination angle toward the condition of the maximum inclination angle is established by the cooperation between the product of inertia of the rotational movement acting in the angle increasing direction during the rotation of the swash plate 16 and the product of inertia based on the urging force of the return spring 26.

The suction chamber 7a in the rear housing 7 is connected to the pre-suction chamber 1d via a suction passage (not shown), the suction chamber 7a being connected to the cylinder bores 1a via suction ports 30 provided through the retainer plate 6, the discharge valve plate 5 and the central valve plate 4, and the suction valve elements. The pre-suction chamber 1d is connected to an evaporator EV in the external refrigerating circuit by piping, and the evaporator EV is connected to a condenser CO via an expansion valve V by piping. The discharge chamber 7b is formed in the rear housing 7 around the suction chamber 7a. The accommodation chamber 7c is formed behind the discharge chamber 7b, and a check valve 33 is accommodated in the accommodation chamber 7c. The accommodation chamber 7c communicates with the muffler chamber 1c of the cylinder block 1 via a discharge passage 7d formed through the retainer plate 6, the discharge valve plate 5, the central valve plate 4 and the suction valve plate 3. The muffler chamber 1c is connected to the condenser CO of the refrigerating circuit by a piping. The discharge chamber 7b communicates with the respective cylinder bores 1a via discharge ports 31, respectively, provided through the central valve plate 4 and the suction valve plate 3. Here, the check valve 33 prevents the coolant gas from flowing in reverse from the condenser CO of the refrigerating circuit and the muffler chamber 1c. In addition, a control valve 32 is arranged in the rear housing 7.

Figure 3:
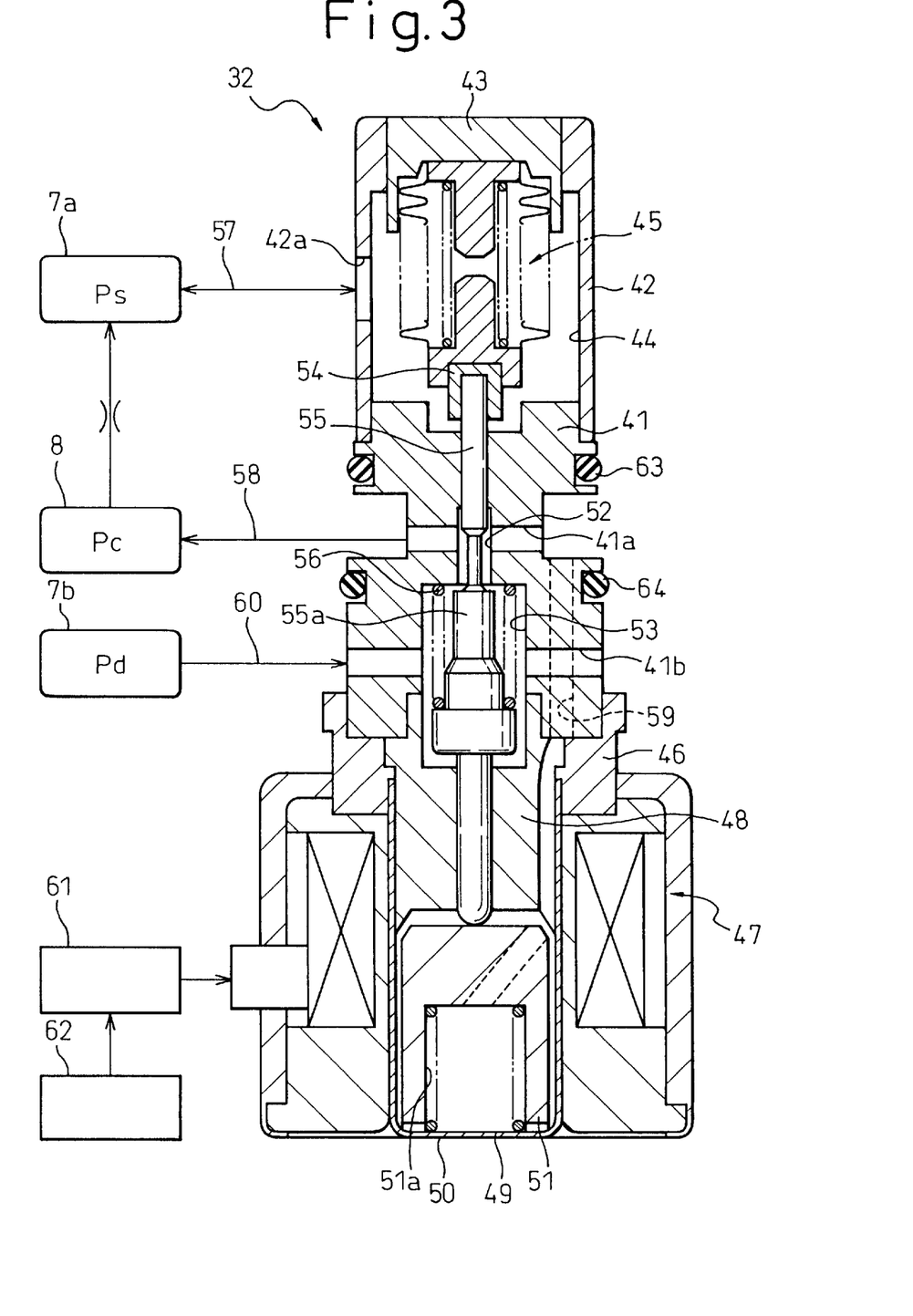
FIG. 3 is a longitudinal sectional front view of the control valve of the variable capacity swash plate type compressor.

As shown in FIG. 3, the control valve 32 has a valve housing 41, a cover 42 is attached to one end of the valve housing 41, and one end of the cover 42 is blocked by a lid member 43. A pressure sensitive chamber 44 is formed in a space defined by the valve housing 41, the cover 42 and the lid member 43, and a bellows 45 is accommodated in the pressure sensitive chamber 44 in the axially extendable and contractible manner.

A solenoid 47 is fixed to the other end of the valve housing 41 via a fixture member 46. A stationary iron core 48 is fixed to the other end of the valve housing 41 in the solenoid 47, and a movable iron core 51 is slidably accommodated in an accommodation tube 49 fixed to the inner wall of the solenoid 47 at the other end of the stationary iron core 48. The movable iron core 51 has a spring chamber 51a, at the other end, in which a spring 50 is disposed for biasing the movable iron core 51 toward the one end.

An axial bore 52 is provided axially through the valve housing 41 and the stationary iron core 48. The axial bore 52 communicates with a valve chamber 53 at a position between the other end of the valve housing 41 and the stationary iron core 48. A rod 55, coupled to the other end of the bellows 45 by a coupling member 54 in the pressure sensitive chamber 44, is slidable in the axial bore 52, and a valve element 55a located within the valve chamber 53 is fixed to an intermediate portion of the rod 55. A spring 56 is provided between the valve element 55a and one end of the valve chamber 53. The other end of the rod 55 abuts against one end of the movable iron core 51.

An opening 42a is provided, in the cover 42, through which the pressure sensitive chamber 44 communicates with the suction chamber 7a of the rear housing 7 via a pressure detection passage 57. Further, in the valve housing 41, a port 41a communicating with the axial bore 52 directing from the valve chamber 53 to the bellows 45 and a port 41b communicating with the valve chamber 53 are formed. The axial bore 52 directed from the valve chamber 53 to the bellows 45 is communicated with the crank chamber 8 by an air-intake passage 58 via the port 41a. Also, the valve housing 41, the stationary iron core 48 and the movable iron core 51 has a cancellation passage 59 for communicating the air-intake passage 58 with the spring chamber 51a in the movable iron core 51. On the other hand, the valve chamber 53 and the discharge chamber 7b of the rear housing 7 are communicated with each other by an air-intake passage 60 via the port 41b. A coil of the solenoid 47 is connected to a control computer 62 via a drive circuit 61. In this regard, reference numerals 63 and 64 denote O-rings for accommodating the control valve 31 within the rear housing 7 in an air-tight manner.

In the thus constructed compressor, as shown in FIGS. 1 and 2, the pulley 22 is rotated by the engine EG via the belt 34 while the engine EG is operating, and the drive shaft 12 is driven. Thus, the swash plate 16 is subjected to a wobbling motion to cause the pistons 19 to reciprocate in the cylinder bores 1a. Therefore, the coolant gas in the evaporator EV in the refrigerating circuit is sucked into the suction chamber 7a of the compressor and then into the cylinder bore 1a, compressed in the cylinder bore 1a, and discharged into the discharge chamber 7b. The coolant gas in the discharge chamber 7b is discharged into the condenser CO via the check valve 33 and the muffler chamber 1c.

While the compressor is operated in this way, the control valve 32 shown in FIG. 3 supplies the coolant gas in the discharge chamber 7b under the discharge pressure (Pd) through the air-intake passage 60, the port 41b, the axial bore 52, the port 41a and the air-intake passage 58, so as to balance the predetermined pressure of the bellows 45 in the pressure-sensitive chamber 44 with the suction pressure (Ps) guided from the suction chamber 7a through the pressure-detection passage 57, under the regulation by the control computer. Accordingly, the pressure (Pc) in the crank chamber 8 is increased or decreased to change the back pressure applied to the pistons 19 and to change the inclination angle of the swash plate 16, whereby the discharge capacity of the compressor is varied from substantially 0% to 100%.

Figure 4:
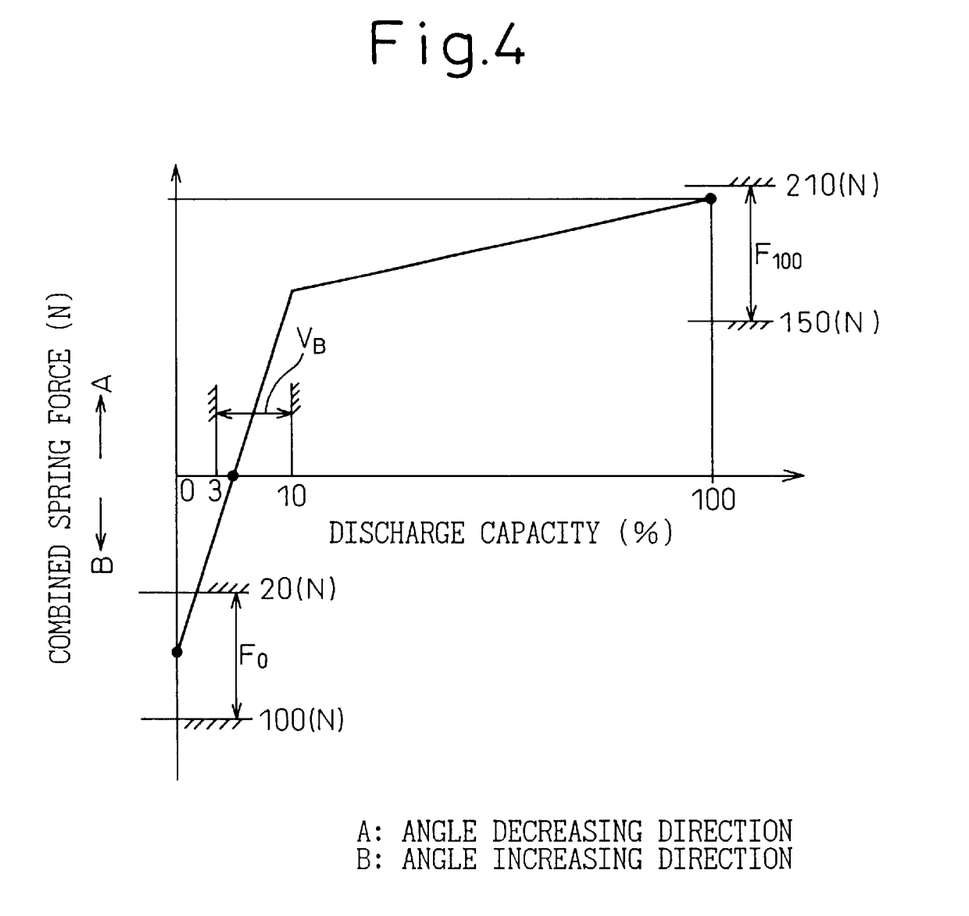
FIG. 4 is a graph illustrating the relationship of the discharge capacity and the combined spring force when the displacement of the compressor is 120 CC.

FIG. 4 illustrates the relationship of the discharge capacity and the combined spring force when the displacement of the compressor is 120 CC. The combined spring force is the sum of the urging force of the angle decreasing spring 17 and the urging force of the return spring 26. The arrow A shows the combined spring force acting on the plus side in which the urging force of the angle decreasing spring 17 is superior to the urging force of the return spring 26 so that the inclination angle of the swash plate 16 is decreased, and the arrow B shows the combined spring force acting on the minus side in which the urging force of the return spring 26 is superior to the urging force of the angle decreasing spring 17 so that the inclination angle of the swash plate 16 is increased. The urging force of the angle decreasing spring 17 balances the urging force of the return spring 26 at a point where the curve crosses the horizontal axis.

In this compressor, as shown in FIG. 4, the discharge capacity becomes 100% when the inclination angle of the swash plate 16 is the maximum inclination angle. In this case, since the displacement ($V_D$) of the compressor is 120 CC, a maximum spring load ($F_{100}$) of the angle decreasing spring 17 applied to the swash plate 16 at the maximum discharge capacity is determined by the following relationship:

$$F_{100}(N) = (180+30) - 4 \times (V_D \times 120) \tag{1}$$

Therefore, the upper limit value is 210N, and the lower limit value is 150N.

In addition, the balance discharge capacity determined by the combined force of the urging force of the angle decreasing spring 17 and the urging force of the return spring 26 when they balance with each other is in the range from 3 to 10% of the maximum discharge capacity. In this case, the minimum spring load ($F_0$) of the return spring 26 applied to the swash plate 16 at the minimum discharge capacity is greater than 20N. The upper limit value of the minimum spring load ($F_0$) is 100N and the lower limit value is 20N.

In this compressor, the compression action of the compressor when the swash plate 16 is at the minimum inclination angle is very low or substantially zero, since the minimum inclination angle of the swash plate 16 is smaller than the limit angle at which the swash plate 16 can assuredly return in the direction to increase the inclination angle by a reaction force of the discharge pressure. Therefore, the power consumption of the engine EG can be reduced.

The swash plate 16 can start rotating at an inclination angle beyond the limit angle so that the swash plate 16 can assuredly return in the direction to increase the inclination angle by a reaction force of the discharge pressure, since the swash plate 16 is urged by the angle decreasing spring 17 in a direction to decrease the inclination angle from the maximum inclination angle to the minimum inclination angle, and also urged by the return spring 26 in the direction to increase the inclination angle from the minimum inclination angle beyond the limit angle, and the urging force of the angle decreasing spring 17 balances with the urging force of the return spring 26 at an angle greater than the limit angle.

According to the result of the experiment conducted by the inventors, as shown in the Table 1 below, the swash plate 16 cannot return in the direction to increase the inclination angle when the load of the return spring 26 is 0N or 10N, but the swash plate 16 can return in the direction to increase the inclination angle when the load of the return spring 26 is 20N. Therefore, it has been found that the operation and the effect described above can be ensured if the minimum spring load ($F_0$) of the return spring 26 applied to the swash plate 16 at the minimum discharge capacity is greater than 20N. The upper limit value of the minimum spring load ($F_0$) is 100N and the lower limit value is 20N.

TABLE 1

| LOAD OF RETURN SPRING (N) | RETURNABILITY |
| --- | --- |
| 0 | x |
| 10 | x |
| 20 | o |

In addition, when refrigeration is not required while the engine EG is operating, the supply of the electric current from the drive circuit 61 to the solenoid 47 in the control valve 32 is interrupted by a command from the control computer 62. Thus, the pressure in the crank chamber 8 increases to change the inclination angle of the swash plate 16 to a minimum level, whereby the stroke of the piston 19 is reduced. As a result, the discharge rate from the cylinder bore 1a into the discharge chamber 7b is reduced, the check valve 33 suppresses the discharge of coolant gas from the compressor, and the compressor is driven at the minimum capacity in the vicinity of zero percent capacity. A small amount of coolant gas is recirculated along a circuit including the cylinder bore 1a, the discharge chamber 7b, the control valve 32, the crank chamber 8, the suction chamber 7a, and the cylinder bore 1a.

On the other hand, when the engine EG is stopped, the drive shaft 12 is stopped and the control valve 32 becomes inoperative. In the check valve 33, the high pressure coolant gas prevailing on the side of the condenser CO is prevented from flowing in reverse into the discharge chamber 7b. In the compressor, the effect of assuredly returning the swash plate 16 in the direction to increase the inclination angle is remarkable, since the discharge chamber 7b is connected to the refrigerating circuit via the check valve 33. Since the compressor provided with the check valve 33 is capable of preventing the coolant gas from flowing in reverse when the compressor is stopped, storage of the liquid coolant within the compressor is avoidable which, in turn, prevents an excessive increase in the pressure or temperature in the compressor, to improve the durability of the compressor.

When the engine EG is started again, the drive shaft 12 is driven and the control valve 32 is operated. The check valve 33 discharges the high pressure coolant gas form the discharge chamber 7b into the condenser CO.

The compressor is constructed in a clutchless manner and the power is transmitted to the compressor as long as the engine EG is being operated. The effect of reducing the power consumption is thus remarkable, and there is also an effect of reducing the weight.

Therefore, the compressor according to the present invention can realize not only a reduction in the power consumption but also the assure the return to a suitable inclination angle, as well as a reduction in the manufacturing cost.

What is claimed is:

1. A variable capacity type compressor comprising:
   a housing having cylinder bores, a crank chamber, a suction chamber, and a discharge chamber formed therein;
   pistons reciprocatingly arranged in said cylinder bores;
   a drive shaft rotatably supported by the housing and driven by an external drive source;
   a swash plate supported by said drive shaft so that said swash plate is rotatable with said drive shaft and can incline with respect to said drive shaft to convert the rotation of said drive shaft into reciprocating motion of said pistons;
   a device controlling the pressure in said crank chamber for changing a discharge capacity from said cylinder bores to said discharge chamber by the reciprocating motion of the pistons based on an inclination angle of said swash plate;
   said swash plate being able to incline between a minimum inclination angle and a maximum inclination angle, said minimum inclination angle being smaller than a limit angle;
   an angle decreasing spring urging said swash plate so as to decrease the inclination angle of said swash plate from said maximum inclination angle toward said minimum inclination angle;
   a return spring urging said swash plate so as to increase the inclination angle of said swash plate from said minimum inclination angle beyond said limit angle; and
   an urging force of said angle decreasing spring balancing with an urging force of said return spring at an angle greater than said limit angle, a minimum spring load ($F_0$) of said return spring applied to said swash plate at a minimum discharge capacity being greater than 20N.

2. A compressor according to claim 1, wherein said angle decreasing spring is arranged around the drive shaft between a first fixed point and said swash plate, and said return spring is arranged around the drive shaft between a second fixed point and said swash plate, said second fixed point being on the opposite side of said first fixed point with respect said swash plate.

3. A compressor according to claim 2, further comprising a lug plate fixed to the drive shaft in the crank chamber for rotation with said drive shaft, said swash plate being coupled to said lug plate so that said swash plate is rotatable with said lug plate and said swash plate is axially movable with respect to said lug plate, said lug plate providing said first fixed point.

4. A compressor according to claim 3, further comprising a circlip fixed to the drive shaft, said circlip providing said second fixed point.

5. A compressor according to claim 1, wherein the discharge capacity when said urging force of said angle decreasing spring balances said urging force of said return spring is in the range from 3 to 10% of the maximum discharge capacity.

6. A compressor according to claim 1, wherein said compressor is operatively coupled to an external drive source in a clutchless manner.

7. A compressor according to claim 1, further comprising a check valve, said discharge chamber being connected to an external refrigerating circuit via said check valve.

8. A compressor according to claim 1, wherein said device controlling the pressure in said crank chamber comprises a first passage connecting said discharge chamber to said crank chamber, a second passage connecting said suction chamber to said crank chamber, a valve arranged at least one of said first and second passages.

9. A variable capacity type compressor comprising:
- a housing having cylinder bores, a crank chamber, a suction chamber, and a discharge chamber formed therein;
- pistons reciprocatingly arranged in said cylinder bores;
- a drive shaft rotatably supported by the housing and driven by an external drive source;
- a swash plate supported by said drive shaft so that said swash plate is rotatable with said drive shaft and can incline with respect to said drive shaft to convert the rotation of said drive shaft into the reciprocating motion of said pistons;
- a device controlling the pressure in said crank chamber for changing a discharge capacity from said cylinder bores to said discharge chamber by the reciprocating motion of the pistons based on an inclination angle of said swash plate;
- said swash plate being able to incline between a minimum inclination angle and a maximum inclination angle, said minimum inclination angle being smaller than a limit angle at which said swash plate can be assuredly returned in a direction to increase the inclination angle by a reaction force of the discharge pressure;
- an angle decreasing spring urging said swash plate so as to decrease the inclination angle of said swash plate from said maximum inclination angle toward said minimum inclination angle;
- a return spring urging said swash plate so as to increase the inclination angle of said swash plate from said minimum inclination angle beyond said limit angle; and
- an urging force of said angle decreasing spring balancing an urging force of said return spring at an angle greater than said limit angle, a maximum spring load ($F_{100}$) of said angle decreasing spring applied to said swash plate at a maximum discharge capacity being determined by the following relationship:

$$F_{100}(N) = (180 \pm 30) - 4 \times (V_D - 120) \tag{1}$$

where $V_D$ is a displacement of the compressor.

10. A compressor according to claim 9, wherein said angle decreasing spring is arranged around the drive shaft between a first fixed point and said swash plate, and said return spring urging said swash plate is arranged around the drive shaft between a second fixed point and said swash plate, said second fixed point being on the opposite side of said first fixed point with respect said swash plate.

11. A compressor according to claim 10, further comprising a lug plate fixed to the drive shaft in the crank chamber for rotation with said drive shaft, said swash plate being coupled to said lug plate so that said swash plate is rotatable with said lug plate and said swash plate is axially movable with respect to said lug plate, said lug plate providing said first fixed point.

12. A compressor according to claim 11, further comprising a circlip fixed to the drive shaft, said circlip providing said second fixed point.

13. A compressor according to claim 9, wherein the discharge capacity when said urging force of said angle decreasing spring balances said urging force of said return spring is in the range from 3 to 10% of the maximum discharge capacity.

14. A compressor according to claim 9, wherein said compressor is operatively coupled to an external drive source in a clutchless manner.

15. A compressor according to claim 9, further comprising a check valve, said discharge chamber being connected to an external refrigerating circuit via said check valve.

16. A compressor according to claim 9, wherein said device controlling the pressure in said crank chamber comprises a first passage connecting said discharge chamber to said crank chamber, a second passage connecting said suction chamber to said crank chamber and a valve arranged at least one of said first and second passages.

\* \* \* \* \*

UNITED STATES PATENT AND TRADEMARK OFFICE
CERTIFICATE OF CORRECTION

PATENT NO. : 6,425,741 B1
DATED : July 30, 2002
INVENTOR(S) : Mera et al.

It is certified that error appears in the above-identified patent and that said Letters Patent is hereby corrected as shown below:

Column 8,
Line 44, delete "+" and insert therefor -- ± --.

Column 10,
Line 6, delete "the" (first occurrence).

Signed and Sealed this

Thirty-first Day of December, 2002

JAMES E. ROGAN
*Director of the United States Patent and Trademark Office*